United States Patent [19]  [11]  4,150,233
Chadwick [45] Apr. 17, 1979

[54] WATER-SOLUBLE TETRAPHENYLPYRIDINIUM SALT FOR USE AS AN ANALYTICAL REAGENT

[76] Inventor: Thomas C. Chadwick, 625 Angela Ct., Santa Maria, Calif. 93454

[21] Appl. No.: 797,004

[22] Filed: May 16, 1977

[51] Int. Cl.$^2$ ............................................. C07D 213/20
[52] U.S. Cl. .................................. 546/342; 546/346; 546/347; 23/230 R
[58] Field of Search ......... 260/290 HL, 290 R, 295 S

[56] References Cited
PUBLICATIONS

Lukes et al., Chem. Abstracts, vol. 42, No. 16, p. 6694f–g Aug. 20, 1948.
Chadwick, Chem. Abstracts, vol. 85, No. 8, item No. 54,153a Aug. 23, 1976.

Primary Examiner—Alan L. Rotman

[57] ABSTRACT

This invention relates to a new water-soluble, tetraphenyl substituted pyridinium salt compound and to a novel process of producing it. This compound finds use as a selective analytical reagent for certain large anions of low charge density.

4 Claims, No Drawings

WATER-SOLUBLE TETRAPHENYLPYRIDINIUM SALT FOR USE AS AN ANALYTICAL

BRIEF SUMMARY OF THE INVENTION

Heretofore, chemical reagents such as Nitron, tetraphenylarsonium chloride, and water-soluble tetraphenylphosphonium and -stibonium salts which are useful for the separation of anions by solvent extraction or precipitation have been difficult and expensive to prepare. Despite the existance of these previously mentioned reagents, a need has existed for inexpensive, easily prepared reagents.

The pertinent literature regarding existing anion reagents is set out in the following references:

D. F. Boltz, "CRC-Critical Reviews in Analytical Chemistry," L. Meites and B. M. Campbell, Eds., CRC Press, Cleveland, Ohio, 1973, pp. 147–199.

F. J. Welcher, "Organic Analytical Reagents," Vol. I, II, III, IV, D. Van Nostrand Company, New York, N.Y., 1947, 1948.

A. J. Bowd, E. Thorburn Burns, and A. G. Fogg, Talanta, 16, 719 (1969).

J. L. Lambert, and W. A. Joern, J. Chem. Ed., 49, 735, (1972).

In none of the literature reviewed is mention made of either the synthesis or use of tetraphenylpyridinium acetate as a reagent for the separation or concentration of anions by either precipitation or solvent extraction. Similarly, there is no mention in the literature of the synthesis of pyridinium salts by the reaction of 1,3,5-triphenyl-2-penten-1,5-dione with aniline in the presence of acetic acid.

The present invention resides in the discoveries that 1,2,4,6-tetraphenylpyridinium acetate is easily synthesized by novel means from readily accessible 1,3,5-triphenyl-2-penten-1,5-dione and aniline in the presence of acetic acid and further that said pyridinium cation is quite soluble in aqueous solution when combined with an anion such as acetate, but said pyridinium cation forms salts with certain large anions which are insoluble in aqueous solution but are soluble in certain organic, water imiscible solvents.

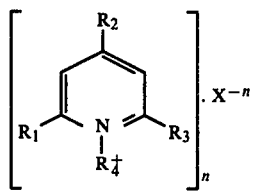

The ready availability of this compound is made possible by the discovery that it can be made by the following reaction:

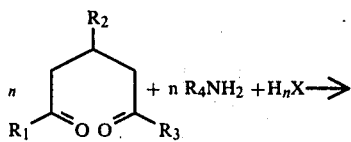

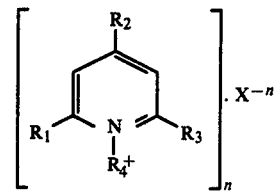

The dienone may be made by methods already described in the literature. In this regard attention is directed to Anal. Chem., 46, 1326 (1974), which is incorporated herein by reference.

DETAILED DESCRIPTION OF THE INVENTION

The pyridinium salt is made in a solution of acetic acid which not only supplies the anion but simultaneously serves as catalyst and solvent. The amount of acid used is the smallest amount that will allow the reaction to proceed at a reasonable rate at approximately 100° C., and since the acid also supplies the anion, the absolute lower limit of acid is set by the amount demanded by the stoichiometry of the reaction.

Although the reaction will proceed over a range of temperatures, it has been found convenient to conduct the reaction approximately 100° C. The reaction is complete in one hour at that temperature.

Normally the product is not isolated but is obtained instead in aqueous solution. The excess acid may either be neutralized to its corresponding salt with a convenient base such as one of the alkali or alkaline earth metal hydroxides, oxides, or carbonates, or the acid may be left unneutralized. The acetate salt may be isolated by adding a large excess of a metal acetate salt to the aqueous solution of pyridinium salt and upon addition of the metal acetate the pyridinium salt separates as an oil. Since the oily pyridinium salt is difficult to handle it is usually not isolated. Furthermore, the pyridinium salt is normally used in aqueous solution and its isolation serves no purpose.

The water-soluble pyridinium salt described hereinabove can form water-insoluble salts, which are analytically useful, with a select group of large anions of low charge density. Examples of this group would include $ClO_4^-$, $BF_4^-$, $ReO_4^-$, $AuX_4^-$, $I^-$, $PtX_6^{-2}$ (X is a halogen) and anions such as trichloroacetate and 5-sulfosalicylate. The general equation for the reaction for insoluble salt formation is shown below:

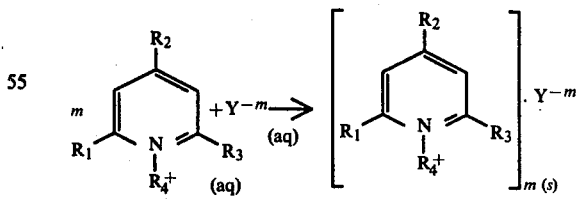

wherein the subscripts (s) and (aq) denote 'solid' and 'aqueous solution' respectively and m denotes the charge on anion Y. Salt formation is straightforward and generally involves only the addition of an amount of water-soluble pyridinium salt in slight excess of the stoichiometric equivalent to an aqueous solution of the anion of interest followed by collection of the resulting insoluble salt by filtration. In many cases this salt formation may be used to good advantage analytically to selectively determine certain anions. For example, perchlorate may be determined in the presence of excess chloride and perrhenate may be determined in the presence of excess tungstate and molybdate. It should be realized that while the reactions being described are useful as analytical separations they might also be used on an industrial scale with no modification whatever save for the size changes.

The following examples are illustrative of compounds and processes of the present invention. Percentages refer to mole percentages unless otherwise specified. The reactions in these examples are generally carried out in a large erlenmeyer flask equipped with a thermometer.

EXAMPLE I

Preparation of 1,2,4,6-Tetraphenylpyridinium Acetate

A. Preparation of 2,4,6-Triphenylpyrylium Bisulfate

In a 2 liter erlenmeyer flask, place 223.04 g of acetophenone and mix well with 134.0 g of benzaldehyde which is known to be free of benzoic acid. Cool the mixture in an ice bath and add 200 g of concentrated sulfuric acid in small portions with vigorous stirring. After the addition of acid is complete, place the flask in a boiling water bath and heat for approximately six hours. After heating, the reaction mixture is worked up by adding approximately 1200 ml of hot distilled water to the mixture in the flask. The organic layer is broken up with a stirring rod and the mixture is brought to a boil to dissolve the pyrylium bisulfate product. The aqueous solution of the pyrylium salt is then separated from the oily reaction byproduct by filtration through coarse filter paper. The aqueous phase is allowed to cool whereupon crystals of product separate. Yields of 2,4,6-triphenylpyrylium bisulfate are generally between 139 and 151 g. The product may be dried at 70° C. without decomposition. Elementary composition and neutralization equivalent confirm the structure.

B. Preparation of 1,3,5-Triphenyl-2-penten-1,5-dione

A 13 to 15 g portion of crude 2,4,6-triphenylpyrylium bisulfate is dissolved in 75 ml of hot water and 100 ml of industrial grade isopropanol is added to the solution. The mixture is heated to dissolve the pyrylium salt whereupon the solution is titrated with 6 N NaOH until the yellow of the pyrylium salt is discharged. If the titration is carried out to a point where the red anion of the diketone is formed, a drop or two of glacial acetic acid is added to dispel the red color. The reaction mixture should be white or cream color at this point and should show no trace of yellow. The walls of the flask are washed down with 25 to 50 ml of water and the flask is then chilled in a refrigerator prior to collection of the product by suction filtration. The product should be suspended in several portions of distilled water to remove sodium sulfate and then dried to yield the crude diketone. Recrystallization of the crude diketone may be carried out in anhydrous isopropanol (use 8 to 10 ml/g of crude diketone). The identity of the product is confirmed by comparison of its melting point with that of a sample prepared by an accepted literature method which is set out in the following reference:

J. A. Berson, J. Am. Chem. Soc., 74, 358 (1952).

C. Preparation of 1,2,4,6-Tetraphenylpyridinium Acetate

In a suitable container (erlenmeyer flasks are suitable but any other vessel which may be heated could serve as well) place 33.33 g of recrystallized 1,3,5-triphenyl-2-penten-1,5-dione and 9.31 g of purified aniline. To this mixture add 37.5 ml of glacial acetic acid and heat on a steam bath or other suitable heating source for two hours. At the end of the heating period add 650 ml of distilled, deionized water and then add 6 N NaOH slowly with extremely rapid stirring. Discontinue the addition when the pH, indicated by a glass electrode, reaches 7.0. Allow any precipitate to settle, collect the supernate by filtration and retain this filtrate. Allow the filtrate to stand for a day, and then filter with 2 g of activated carbon by gravity through a tight filter paper to produce a decolorized filtrate. After determination of the 1,2,4,6-tetraphenylpyridinium acetate concentration (vide infra) dilute the solution to the desired concentration with distilled, deionized water. The 1,2,4,6-tetraphenylpyridinium cation is characterized through its perchlorate and perrhenate salts by elemental analysis.

D. Gravimetric Determination of 1,2,4,6-Tetraphenylpyridinium Acetate Concentration by Precipitation of the Pyridinium Cation as the Perchlorate Dilute a 25.00 ml aliquot of 1,2,4,6-tetraphenylpyridinium acetate solution ($\sim$0.1 M) to 100.0 ml and take 20 ml aliquots for analysis. Dilute each aliquot to approximately 100 ml, add 0.60 g NaCl and then add 4.5 ml of 0.5 M NaClO$_4$ with stirring to precipitate the perchlorate salt. Let stand for several hours and then collect the precipitate on a medium fritted glass filtering crucible. Reuse the mother liquor to transfer most of the solid to the crucible. Wash with a saturated aqueous 1,2,4,6-tetraphenylpyridinium perchlorate solution and then dry at 110° C. for one hour. Weigh the precipitate and obtain the molarity of the solution by multiplying the precipitate weight in milligrams by the factor $4.133 \times 10^{-4}$.

EXAMPLE II

Use of 1,2,4,6-Tetraphenylpyridinium Acetate as a Gravimetric Reagent for Perchlorate and Perrhenate

A. Gravimetric Determination of Perchlorate

An aliquot containing 8 to 80 mg of perchlorate anion is transferred to a beaker and mixed with enough distilled water to bring the volume to 80 ml. Add 0.59 g NaCl and then add a 10% excess of 1,2,4,6-tetraphenylpyridinium acetate solution ($\sim$0.1 M) with constant stirring. The mixture is allowed to stand several hours prior to collecting the precipitate on a fritted glass crucible. The precipitate is washed with a saturated solution of 1,2,4,6-tetraphenylpyridinium perchlorate and dried at 110° C. for one hour prior to weighing. The gravimetric factor for perchlorate anion is 0.2055.

B. Gravimetric Determination of Rhenium as Perrhenate Anion

An aliquot containing 12 to 40 mg of perrhenate is mixed with 0.59 g NaCl and sufficient water to bring the volume of the solution to 95 ml. If tungsten or molybdenum (as $WO_4^{-2}$ or $MoO_4^{-2}$, respectively) are present, 6 ml of concentrated ammonium hydroxide are added. The perrhenate anion is precipitated by adding an amount of 0.1 M 1,2,4,6-tetraphenylpyridinium acetate solution that is 10% in excess of the amount of perrhenate suspected to be present. After at least two hours the precipitate is collected on a fritted glass crucible, washed with 25 ml of saturated 1,2,4,6-tetraphenylpyridinium perrhenate solution and three 25 ml portions of ice water and dried at 110° C. for one hour prior to weighing. The gravimetric factor for perrhenate is 0.3942.

I claim:

1. The compound 1,2,4,6-tetraphenylpyridinium acetate.

2. The compound according to claim 1 in solution in a solvent.

3. A method for the synthesis of the water-soluble pyridinium salt of claim 1, comprising the mixing of aniline, 1,3,5-triphenyl-2-penten-1,5-dione and acetic acid, heating the resulting mixture for a time necessary to complete the formation of the product, and work up of the reaction mixture by dilution with a solvent.

4. The method according to claim 3 wherein workup of the reaction mixture by dilution with a solvent is followed by neutralizaton with a base from the group comprising carbonates, oxides, or hydroxides of the group 1a and 2a elements.

* * * * *